United States Patent
Niva

(10) Patent No.: US 8,069,942 B2
(45) Date of Patent: Dec. 6, 2011

(54) DRIVELINE ON TRUCK

(75) Inventor: Karl-Erik Niva, Kiruna (SE)

(73) Assignee: Atlas Copco Rock Drills AB, Orebro (SE)

( * ) Notice: Subject to any disclaimer, the term of this patent is extended or adjusted under 35 U.S.C. 154(b) by 448 days.

(21) Appl. No.: 12/227,427

(22) PCT Filed: May 30, 2007

(86) PCT No.: PCT/SE2007/050379
§ 371 (c)(1),
(2), (4) Date: Nov. 17, 2008

(87) PCT Pub. No.: WO2007/145582
PCT Pub. Date: Dec. 21, 2007

(65) Prior Publication Data
US 2009/0253547 A1 Oct. 8, 2009

(30) Foreign Application Priority Data
Jun. 13, 2006 (SE) ...................................... 0601295

(51) Int. Cl.
*B60K 17/35* (2006.01)
(52) U.S. Cl. ........ 180/235; 180/6.64; 180/265; 280/400
(58) Field of Classification Search ................. 180/6.54, 180/6.64, 235, 418, 264, 265; 280/400, 442
See application file for complete search history.

(56) References Cited

U.S. PATENT DOCUMENTS

| 5,366,042 A * | 11/1994 | Wilks et al. ................... 180/253 |
| 6,009,969 A | 1/2000 | Salcher et al. |
| 6,039,133 A * | 3/2000 | Zulu ........................... 180/6.64 |
| 6,174,255 B1 | 1/2001 | Porter et al. |
| 6,336,069 B1 | 1/2002 | Hasegawa et al. |
| 6,357,315 B1 * | 3/2002 | Smith et al. ................ 74/473.11 |
| 6,631,320 B1 * | 10/2003 | Holt et al. ....................... 701/83 |
| 7,766,104 B2 * | 8/2010 | Newberry et al. ......... 180/24.09 |
| 2002/0027025 A1 * | 3/2002 | Kobayashi et al. ............ 180/6.2 |
| 2003/0216212 A1 | 11/2003 | Rodeghiero |

FOREIGN PATENT DOCUMENTS

| JP | 2003237619 A * | 8/2003 |
| SU | 528224 | 9/1976 |
| SU | 1493498 | 7/1989 |
| WO | WO 0249896 | 6/2002 |

* cited by examiner

Primary Examiner — Joanne Silbermann
Assistant Examiner — Maurice Williams
(74) Attorney, Agent, or Firm — Mark P. Stone

(57) ABSTRACT

A device and a method for engaging and disengaging a longitudinal differential (10) disposed between a forward wheelshaft (4) and a rear wheelshaft (5) of an articulated vehicle (1) which has a front element (2) and a rear element (3) pivotable about a steering linkage (6) disposed between them and which comprises a distribution box (9) which supplies power from an engine (7) to the forward wheelshaft (4) in the front element (2) via a first shaft (11) and to the near wheelshaft (5) in the rear element (3) via a second shaft (12), wherein the longitudinal differential (10) is disposed between the first shaft (11) and the second shaft (12), whereby a steering angle v formed between the front element (2) and the rear element (3) is detected by a detection means (25a) so arranged that the detection means (25a) causes a differential brake (20) for the longitudinal differential (10) to be kept locked, or braked, when the detection means (25a) detects a steering angle v which is smaller than a predetermined steering angle $V_1$.

13 Claims, 5 Drawing Sheets

DRIVELINE ON TRUCK

TECHNICAL FIELD

The present invention relates to a device and a method for an articulated vehicle, particularly an articulated mine loader, comprising a front element and a rear element which are pivotable about a steering linkage disposed between them, where a differential disposed between a wheelshaft in the front element and a wheelshaft in the rear element is locked, or braked, by a brake in response to the occurrence of a predetermined angle between the front element and the rear element.

STATE OF THE ART

A known practice is to provide an articulated vehicle, e.g. a dumper, with drive on all the wheels in order to achieve good capability for negotiating soft and/or slippery surfaces. To this end, a driveline of the vehicle includes a forward wheelshaft arranged in the vehicle's front element. The forward wheelshaft has a forward transverse differential powered via a first driveshaft starting from a distribution box usually situated in the front element for powering the right and left front wheels. A rear wheelshaft is situated in the vehicle's rear element. To power the right and left rear wheels, the rear wheelshaft likewise has a transverse differential, a rear transverse differential, which is powered via a second driveshaft from the distribution box. The vehicle may also have more than one rear axle powered in a similar manner. The distribution box receives its power via a transmission shaft which starts from a gearbox situated close to an engine in the front element, whereby the distribution box distributes torque to forward and rear wheelshafts.

The forward and rear transverse differentials make it possible for wheels on one and the same shaft to travel different distances during vehicle cornering, by the front element and the rear element being subjected to a steering angle so that they form an angle to one another, which means that the respective longitudinal axes of the front element and the rear element form an angle with one another. This technique works perfectly well so long as the wheels have a good grip on the running surface, but if the grip of the wheel on a wheelshaft deteriorates while the differential is open (i.e. when the differential is not locked), the wheel will begin to slip (Of course, this only happens in cases where there is a longitudinal differential and it is open. In the case of a distribution box with no differential, the driveshafts will cause the front and rear axles to rotate at the same speed. For slipping to be possible, one of the driveshafts has to be able to rotate faster.) and power from the engine will accordingly be directed to the slipping wheel. A consequence of this is that it is the slipping wheel which determines the combined drive power on the respective wheelshaft. In view of the disadvantages described, a differential lock is usually provided to make it possible in such situations to lock the transverse differential and thereby cause the wheels to rotate at the same speed. For this reason, a differential is not usually installed on mine loaders of a corresponding kind.

Another known technical practice is to provide a differential on longitudinal shafts so that the drive power which the aforesaid forward and rear driveshafts receive from the distribution box is standardised via a differential (hereinafter called the longitudinal differential) as described above. This is done with a view to making it possible for wheels on the forward wheelshaft and the rear wheelshaft to travel different distances during vehicle cornering. Here again, such a longitudinal differential works satisfactorily so long as all of the vehicle's wheels have a good grip, but if the grip of wheels on a wheelshaft deteriorates (usually wheels of the front element in the case of a laden vehicle), which commonly occurs on steep slopes, e.g. in the case of mine loaders, the wheel/wheels on that wheelshaft will begin to slip and power from the engine will be directed to the slipping wheel or wheels on the wheelshaft with the poorer grip if the vehicle has a transverse differential on the axle concerned and the differential is open. To prevent such slipping, the longitudinal differential may also be provided with a differential lock making it possible to lock the differential so that the respective shafts powering the forward and rear wheelshafts rotate at the same speed. The result will be that all of the wheels on the same wheelshaft rotate at the same speed. For the reasons here described, it is likewise usual for articulated mine loaders not to be equipped with a longitudinal differential.

A particularly clear disadvantage occurs in articulated vehicles/trucks, e.g. a mine loader or dumper, which have a front element adapted to pivoting about a vertical steering linkage about which the rear element is also adapted to pivoting. On such a vehicle, the forward wheelshaft and the rear wheelshaft are usually arranged at different distances from said steering linkage. The forward wheelshaft is usually fitted at a substantially shorter distance from the steering linkage. This configuration results in the two wheelshafts running at completely different radii of curvature during vehicle cornering. If such a vehicle negotiates a curve with the longitudinal differential locked, particularly if the vehicle is carrying a heavy load on the rear element, on a ground surface where the wheels grip well, the transmissions, particularly the driveshafts and distribution box, will be subject to very severe loads in the form of retarding torque because wheels on the forward wheelshaft will tend to rotate faster than corresponding wheels on the rear wheelshaft. In addition to the stresses on transmissions, there will be increased tyre wear and driving will be more difficult, since the vehicle will understeer and tend to travel straight ahead when cornering. The same disadvantage as here described does of course occur in the case of a corresponding articulated vehicle which has no longitudinal differential, e.g. mine loaders of comparable construction.

A longitudinal differential needs a locking function in order, as described above, to prevent all the torque from the engine being directed to just one axle, whose wheels have low friction relative to a roadway surface. There are known solutions for locking the differential. One such takes the form of a claw coupling which locks the driveshafts once it is engaged. U.S. Pat. No. 6,641,223 refers to a claw coupling solution for an articulated vehicle. A drawback of that solution is that the vehicle has to come to a standstill in response to locking by the claw coupling.

According to another known technique, a percentage braking value ("limited slip") is preset for the longitudinal differential. If the braking value is set too low, torque may still be directed to only one wheelshaft. Too high a looking value will likewise subject the vehicle's driveline transmissions to a high torque. The discs of the differential's brake will wear, thereby also affecting the intended locking action.

U.S. Pat. No. 6,009,969 also provides an example of the state of the art in this field, and US patent specification 2003/0216212 another pertaining to an unarticulated vehicle.

An object of the present invention is to present a solution to the disadvantages described above of the state of the art.

DESCRIPTION OF THE INVENTION

One aspect of the invention presents a device with characteristics according to the attached claim 1.

Another aspect of the invention presents a method with characteristics according to the attached independent method claim.

Other versions of the invention are set out in the dependent claims.

One of the advantages of the solution presented is that the longitudinal differential is normally locked, resulting in maximum vehicle capability, and that the differential brake which locks the longitudinal differential is only disengaged at large steering angles at which abnormally large torque increases occur because of different distances being traveled by the front and rear axles respectively. Such automatic disengagement of the differential brake means that in normal circumstances the driver of the vehicle will not need to consider whether it is necessary to disengage or engage a differential brake. This is particularly advantageous in the case of articulated mine loaders, which commonly have to negotiate slippery surfaces in combination with steep slopes.

Another substantial advantage is that the longitudinal differential system is fail-safe, since any fault occurring in the oil circuits which control the longitudinal differential will automatically result in the system reverting to the longitudinal differential's normal state, i.e. to keeping the differential brake locked.

EMBODIMENTS

A number of embodiments of the invention are described below with reference to the attached drawings.

Figure 1:
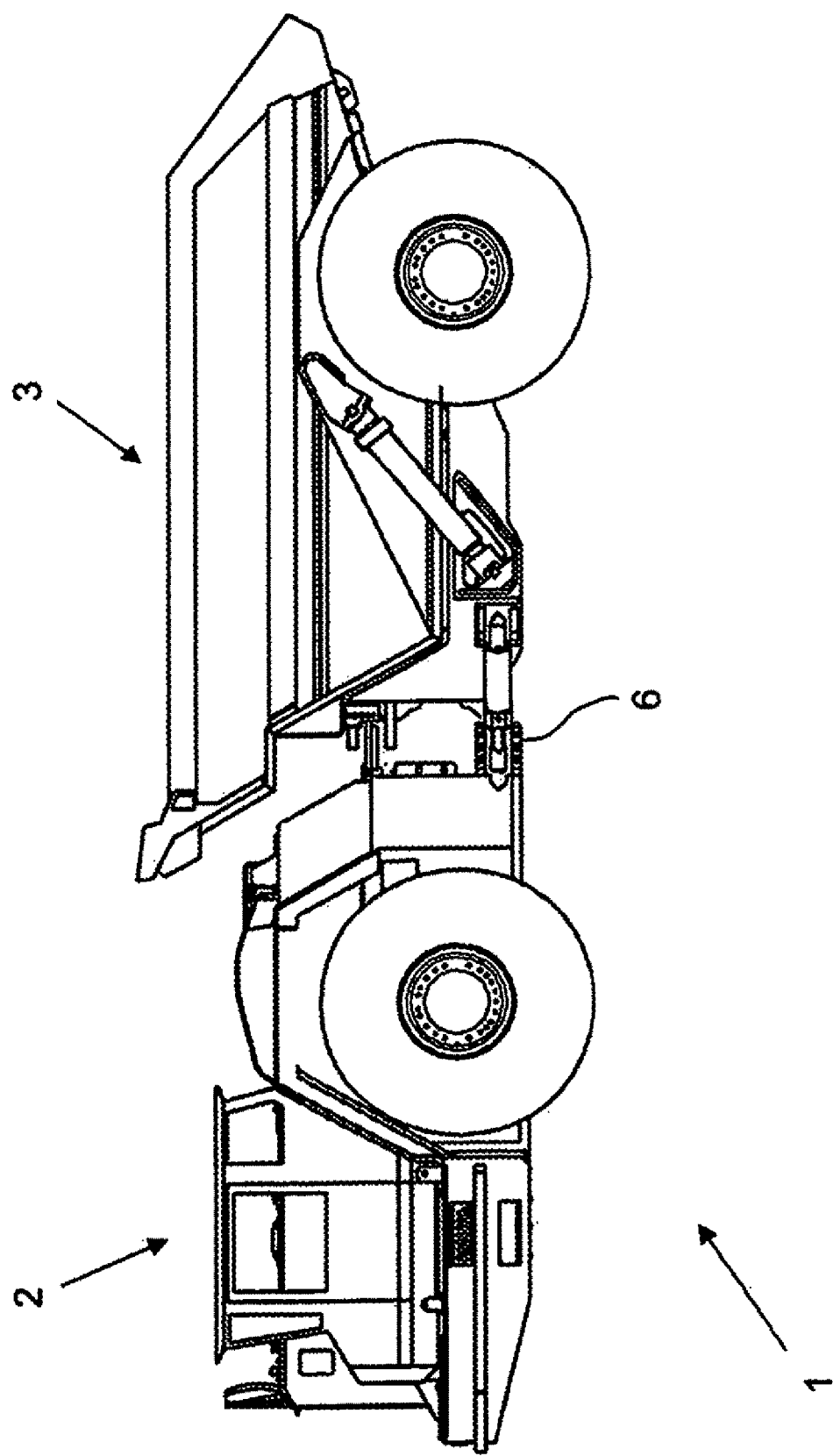
FIG. 1 depicts a schematic side view of an articulated vehicle of the type to which the invention relates.
Figure 2:
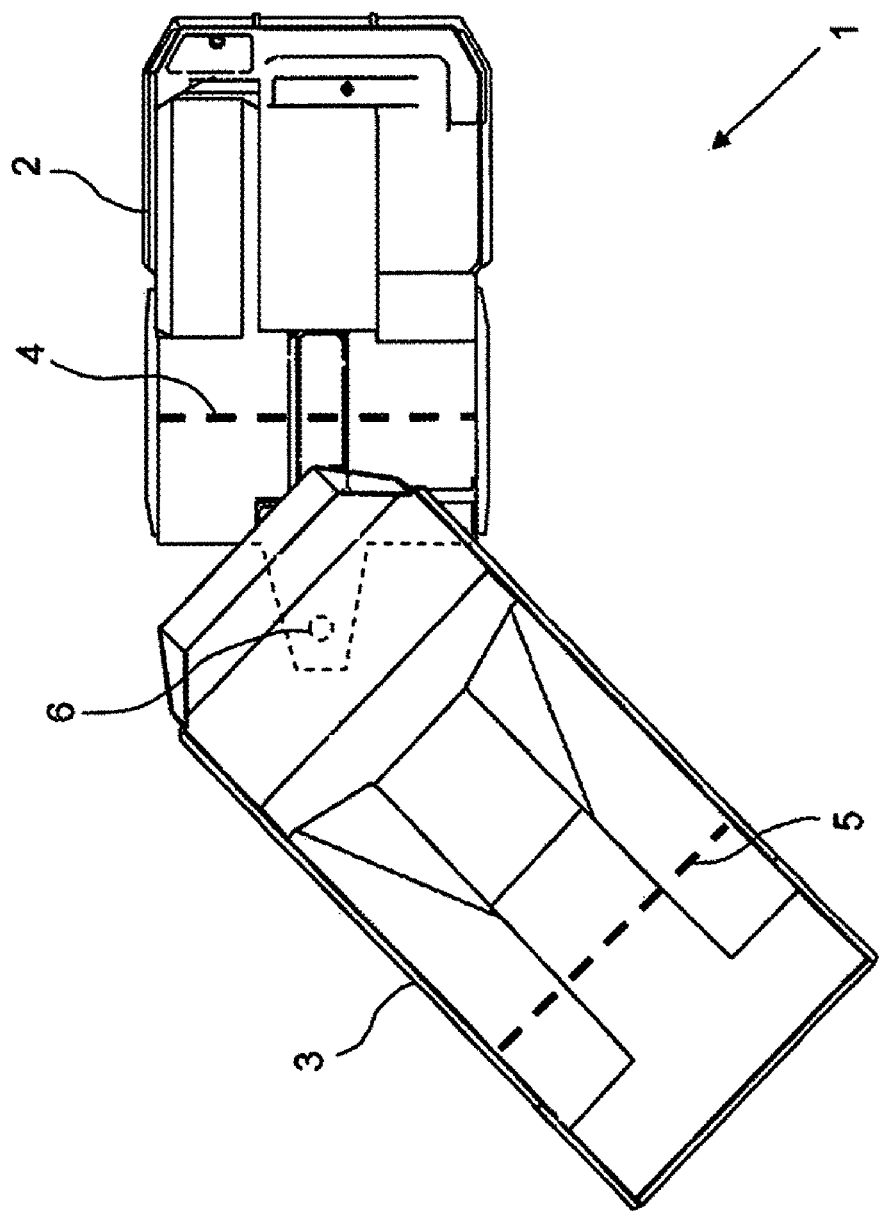
FIG. 2 depicts a schematic plan view of the vehicle according to FIG. 1, with the vehicle's front element and rear element at an angle to one another.

An embodiment of an articulated vehicle of the kind referred to in the present invention is illustrated in FIG. 1. The vehicle is denoted by ref. number 1. The vehicle's front element is denoted by 2 and its rear element by 3. FIG. 2 depicts in plan view from above the articulated vehicle according to FIG. 1, with the steering angle formed between the front element 2 and the element 3. In this embodiment the front element of the vehicle is provided with a forward wheelshaft 4 and the rear element is provided with a rear wheelshaft 5. For the sake of simplicity, the forward wheelshaft 4 and the rear wheelshaft 5 are represented in the diagram by broken lines. The front element 2 can be steered at a steering angle relative to the rear element 3 because the front and rear elements are articulated about a steering linkage 6. As may be seen in FIGS. 1 and 2, the distance between the forward wheelshaft 4 and the steering linkage 6 and the corresponding distance between the rear wheelshaft 5 and the steering linkage 6 are different, resulting in the previously mentioned disadvantages of different distances being traveled by the forward and rear wheelshafts when the articulated vehicle 1 is cornering. The drawings show only one rear wheelshaft but the rear element may of course, if so desired, be provided with two separate wheelshafts powered independently (by the same driveshaft).

Figure 3:
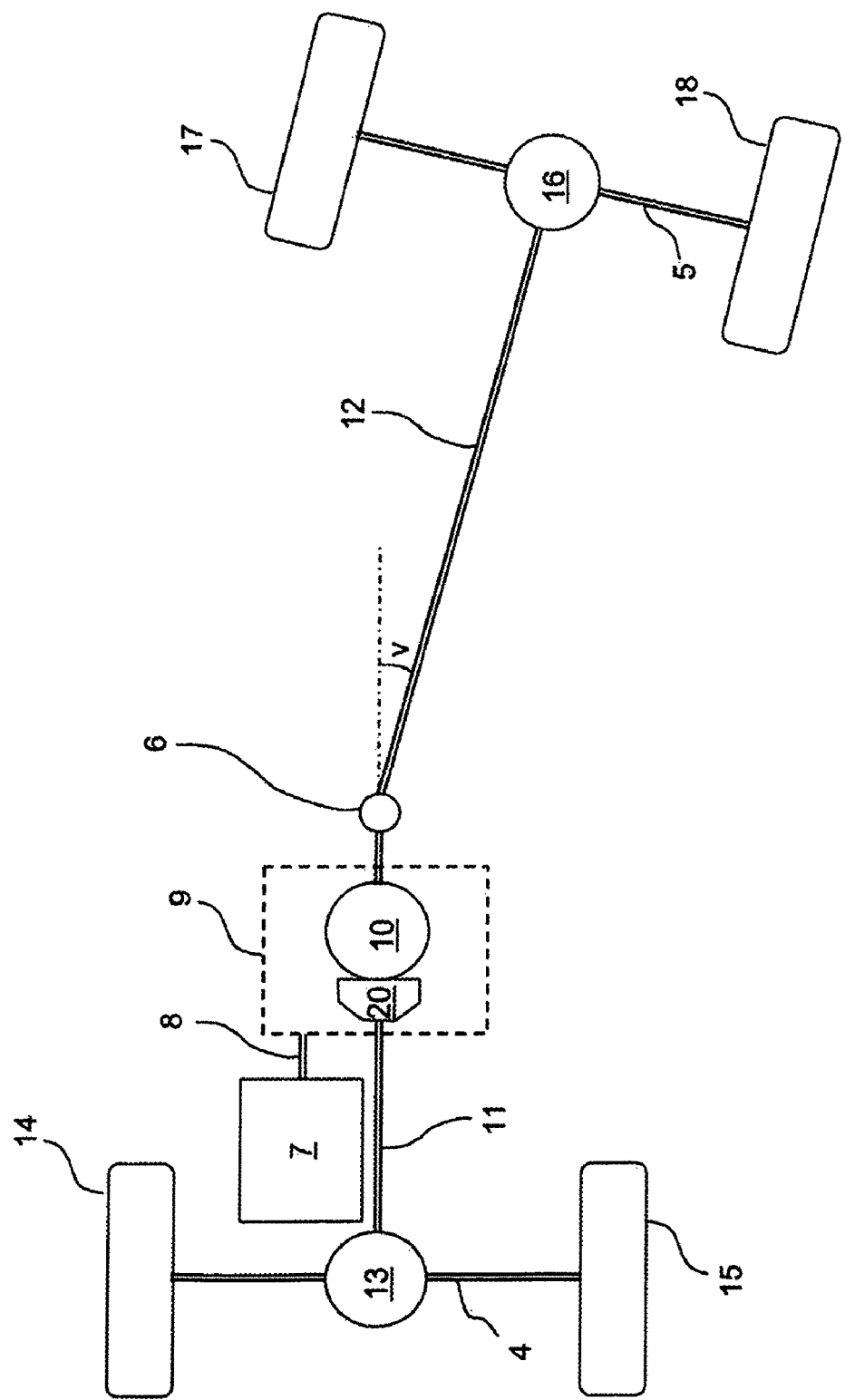
FIG. 3 schematically depicts transmissions for an articulated vehicle according to an aspect of the invention.

FIG. 3 depicts schematically, the main components concerned in the articulated vehicle in one embodiment of the invention. In the embodiment depicted, an engine 7 is situated in the front element of the vehicle. The engine usually takes the form of a diesel engine, but the type of engine is of minor significance for the invention. The engine, ref. 7 in the drawings, also normally includes a gearbox. There is of course nothing to prevent the gearbox being situated elsewhere in the front element. The engine 7 transfers power to an undepicted gearbox which is situated dose to the engine and which transfers torque via an output transmission shaft 8 to transmissions in a distribution box 9. In the embodiment according to this aspect of the invention, the distribution box 9 comprises a differential, hereinafter called the longitudinal differential 10. The longitudinal differential transfers torque to a first shaft 11 intended to power the wheelshaft 4 in the front element 2 and to a second shaft 12 for powering the wheelshaft 5 in the rear element 3.

The power from the first shaft 11 is transferred via a forward transverse differential 13 to the forward wheelshaft 4. A forward right wheel 14 and a forward left wheel 15 on the forward wheelshaft 4 can, when so required, rotate independently of one another in a known manner as a result of the forward transverse differential 13. Power from the second shaft 12 is correspondingly transferred via the steering linkage 6 and a rear transverse differential 16 to the rear wheelshaft 5. A rear right wheel 17 and a rear left wheel 18 on the rear wheelshaft 5 can, when so required, rotate independently of one another in a known manner as a result of the rear transverse differential 16. During vehicle cornering, the first shaft 11 and the second shaft will form a steering angle v with one another. This steering angle v is illustrated in FIG. 3.

According to an aspect of the invention, the longitudinal differential 10 is equipped with a differential brake 20. This differential brake 20 is coupled to the longitudinal differential. The purpose of the differential brake 20 is to brake the longitudinal differential 10, when so desired, so that the first output shaft 11 and the second output shaft 12 rotate locked to one another. When so desired, the differential brake 20 has to be unlockable so that the forward wheelshaft 4 and the rear wheelshaft 5 can rotate at different speeds independently of one another.

Figure 4:
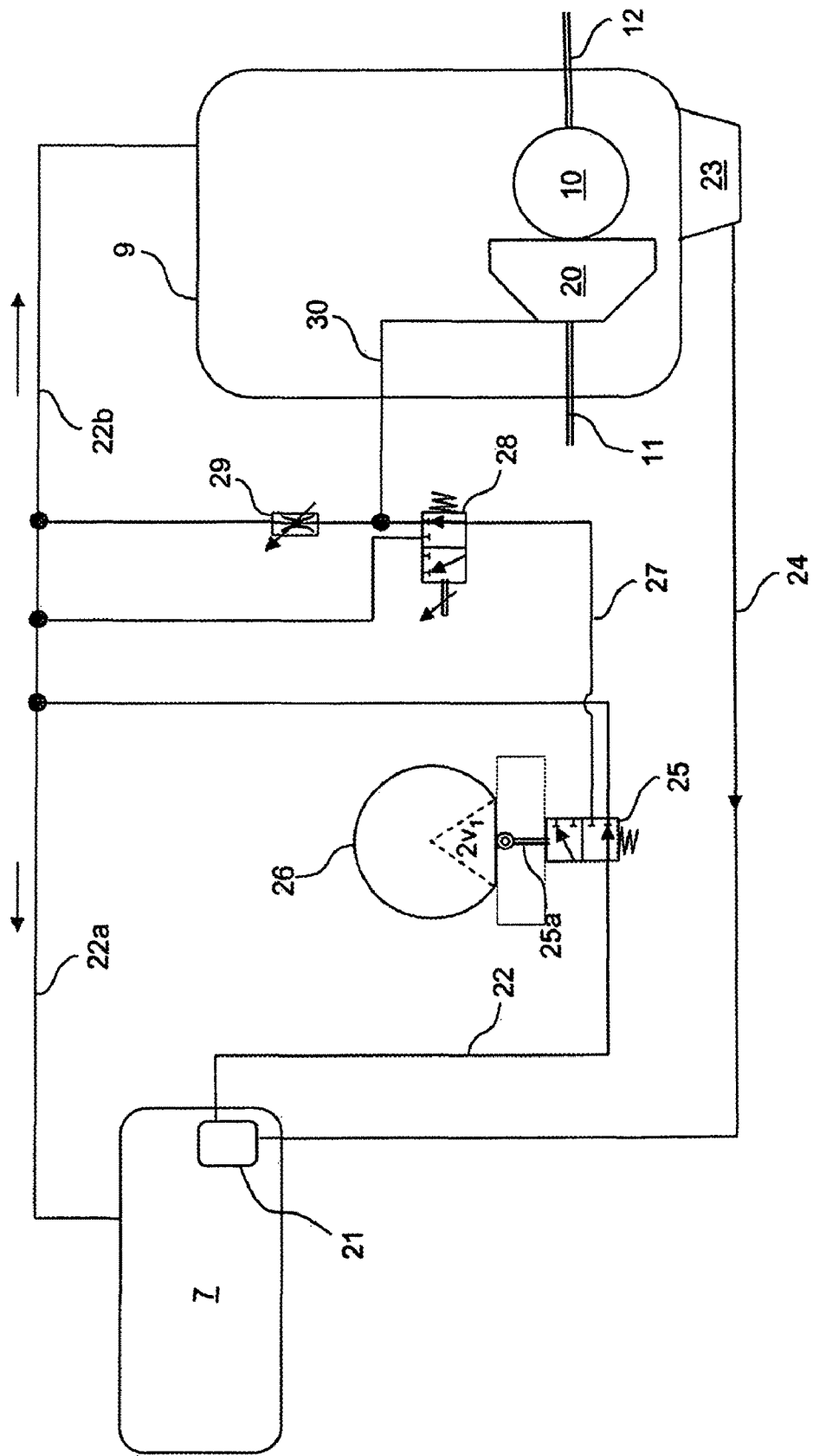
FIG. 4 illustrates a skeleton diagram for control of the longitudinal differential in the vehicle's transmissions according to FIG. 3.

A schematic layout for control of the differential brake 20 is depicted in FIG. 4, which shows the engine 7 driving a hydraulic oil pump 21. The hydraulic oil is used for lubricating both the engine 7 and the distribution box 9 and, for the sake of simplicity, is hereinafter referred to simply as oil. In normal circumstances, i.e. at a predetermined minimum steering angle, the pump 21 pushes the oil through a loop comprising oil conduits 22, 22a, 22b to a transmission of the engine 7 and the distribution box 9 in order to lubricate these units. Oil accumulates in the oil pan 23 under the distribution box 9 and is returned to the pump 21 via a suction conduit 24.

The control of an automatic arrangement for locking the differential brake 20 when a predetermined steering angle $v_1$ occurs can be effected in various ways. An embodiment is depicted in FIG. 4. A control valve 25 is installed in the oil conduit 22 from the pump 21. In this embodiment, the control valve 25 abuts, via a guide roller an operating arm 25a of the valve, against a surface of a steering linkage spindle 26, i.e. against the latter's outer contour. Said steering linkage spindle 26 rotates during cornering with the articulated vehicle 1 at the same angle as the aforesaid steering angle v. The operating arm 25a of the control valve 25 abuts the steering linkage spindle 26 on a planar surface of the latter which extends along a chord of the circle circumference which limits the cross-sectional area of the steering linkage spindle 26 in such a way that said chord cuts off the circle circumference along a sector of the steering linkage spindle 26 at a sector angle which is double $v_1$.

When the guide roller on the operating arm of the control valve 25 bears upon said planar surface on the steering linkage spindle 26, i.e. when the steering angle is rather small, oil will flow in the oil conduits as described above. At a steering angle v=0 the guide roller will be on the planar surface along the sector centre line, but during vehicle cornering in such a way that the steering angle $v_1$ is exceeded, the steering linkage spindle 26 will rotate so that the guide roller on the operating arm of the control valve 25 moves out on the periphery of the steering linkage spindle, with the result that the operating arm of the control valve 26 will be pushed in and cause the latter to change state, causing oil from the pump 21 to be directed through the control valve to a control duct 27.

The oil in the control duct 27 passes through a manually operable valve 28 and proceeds to the previously mentioned oil conduits 22a and 22b for lubrication of the engine and the distribution box via a throttling 29. Between the manually operable valve 28 and the throttling 29 there is a branch for oil to reach a connecting conduit 30. The pressure in this connecting conduit 30 acts upon the differential brake 20. When the pressure in the connecting conduit is low, spring forces acting in a known manner keep discs in contact with one another and thereby connect together the first shaft 11 and the second shaft 12 in the longitudinal differential 10 so that the latter is braked or, in other words, locked. In contrast, high oil pressure in the connecting conduit 30 will act upon a piston in the differential brake to counteract said spring forces so that the discs are freed from one another and the differential brake is disengaged or, in other words, unlocked.

The differential brake will thus be disengaged when the control valve 25 detects a steering angle larger than $v_1$, since the control valve 25 will thereupon change state and the connecting conduit 30 will exert pressure on the piston in the differential brake so that the latter becomes disengaged and the longitudinal differential 10 will operate without braking.

Figure 5:
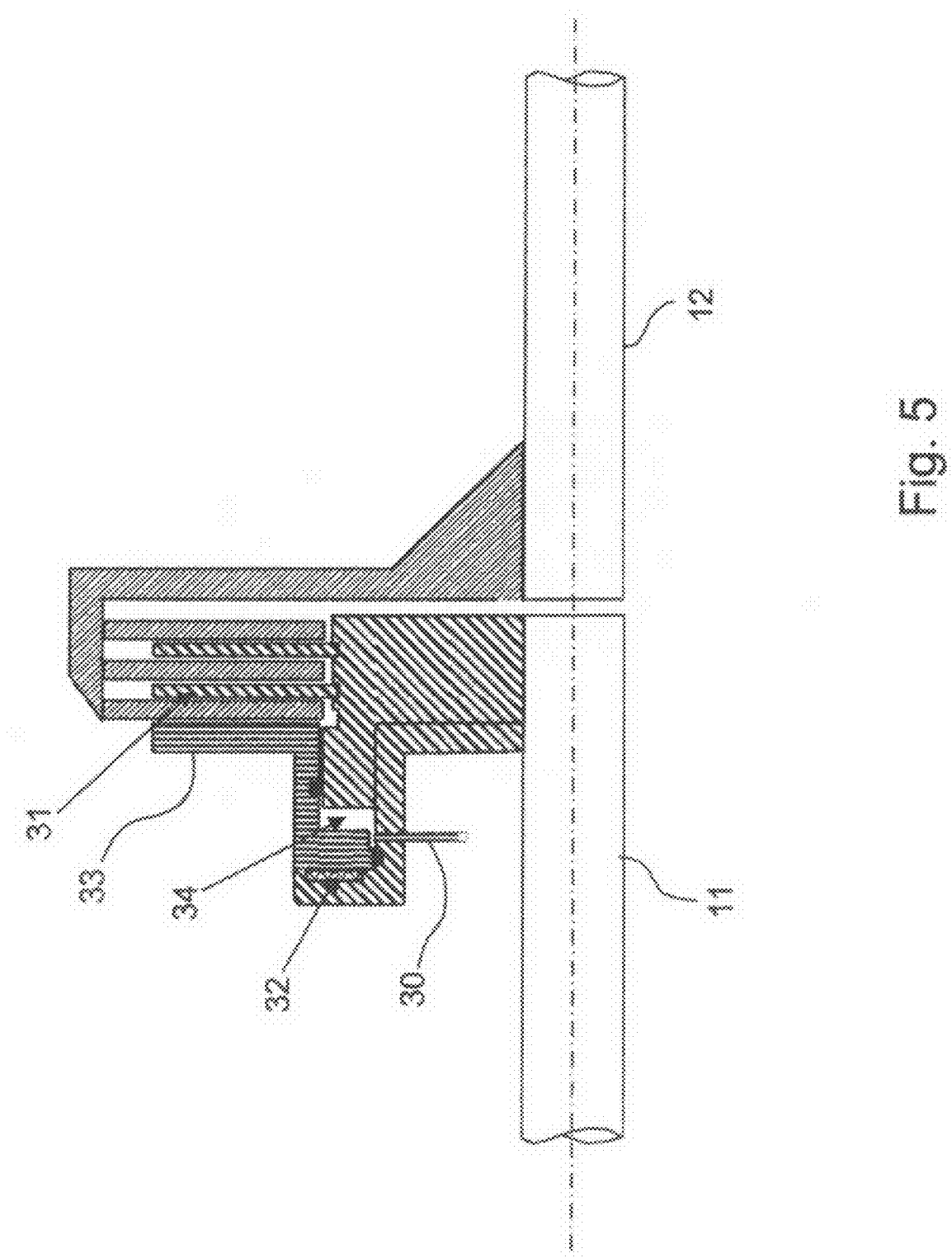
FIG. 5 illustrates, very schematically, a section through an embodiment of a differential brake according to an aspect of the invention.

A very simplified illustration of the differential brake 20 is depicted in FIG. 5, which shows how the first shaft 11 and the second shaft 12 can be coupled together by a disc package 31. When the oil pressure in the connecting conduit 30 is low, a spring package 32 exerts pressure on a piston 33 so that the discs in the disc package 31 are coupled together. In contrast, if the steering angle v is greater than $v_1$, the connecting conduit 30 becomes open to pressure, causing oil pressure to be generated in a chamber 34. The spring force of the spring package 32 is such that the oil pressure in the chamber 34 will cancel out the action of the spring package 32, so that the piston 33 reverts to a neutral position whereby the discs of the disc package 31 are freed from one another and thereby unlock the differential brake 20.

As an embodiment, the throttling 29 may be such that the oil pressure in the conduit upstream of the throttling is 1 bar. Alternatively, a settable throttling may be used in order to allow a certain amount of slipping, in which case a higher pressure upstream of the throttling will be the oil pressure which opens the differential brake 20. If a fault occurs in the oil system whereby the connecting conduit 30 loses its pressure, the differential brake 20 will lock the differential automatically, thereby making the longitudinal differential fail-safe.

The predetermined steering angle $v_1$ which constitutes the steering angle v at which the differential brake 20 is intended to open may be selected according to the use and the roadway surface for which the vehicle is intended. A suitable predetermined steering angle $v_1$ is 20°. At that angle, problems of different roller angles for the forward and rear wheelshafts can be coped with by the vehicle. The predetermined angle $v_1$ selected may of course be different. Suitable alternative values of $v_1$ are 10° to 30°, preferably 15° to 25°.

The manually operable valve 28 is intended to be a valve which can be acted upon by the vehicle's driver so that he/she can revert to locked differential brake 20 even when the differential brake is automatically disengaged, whereby oil will flow in the loop 22, 22a, 22b without being affected by the throttling 29 and pressurisation of the connecting conduit 30.

The invention claimed is:

1. An articulated vehicle (1) comprising:
a front element and a rear element which are pivotable about a steering linkage disposed between them,
a distribution box which supplies power from an engine to a forward wheelshaft of the front element via a first shaft and to a rear wheelshaft of the rear element via a second shaft,
characterised in that
a differential is disposed between the first shaft and the second shaft,
a detection means detects a steering angle v formed between the front element and the rear element,
the detection means detects whether the steering angle v is greater than a predetermined steering angle $v_1$,
a brake is disposed relative to said differential in order to lock, or brake, the differential when the steering angle v is smaller than said predetermined steering angle $v_1$,
wherein the detection means takes the form of an operating arm of a valve, which operating arm is provided with a guide roller which bears upon an outer contour of a spindle of the steering linkage.

2. The vehicle according to claim 1, wherein said predetermined steering angle $v_1$ is between 10° and 30°.

3. The vehicle according to claim 1, wherein the outer contour of the steering linkage spindle in a region which the operating arm bears upon takes the form of a planar surface.

4. The vehicle according to claim 1, wherein the valve takes the form of a hydraulic valve which causes a piston in the differential brake to engage or disengage the differential brake.

5. The vehicle according to claim 4, where the valve switches between allowing high oil pressure or low oil pressure in a connecting conduit supplying oil to the differential brake in order respectively to engage and disengage the differential brake.

6. The vehicle according to claim 5, wherein loss of oil pressure in the connecting conduit causes the differential brake to revert to a locked state, whereby the differential is provided with fail-safe function.

7. The vehicle according to claim 5, wherein said high oil pressure in the connecting conduit is determined by a throttling which is:
preset at a predetermined pressure value or set at a pressure value selected by an operator.

8. The vehicle according to claim 1, wherein the differential brake can be disengaged manually from a locked state by means of a manually operable valve.

9. The vehicle according to claim 1, wherein said predetermined steering angle is between 15 degrees and 25 degrees.

10. The vehicle according to claim 1, wherein said predetermined steering angle is 20 degrees.

11. A method for engaging and disengaging a longitudinal differential disposed between a forward wheelshaft and a rear wheelshaft of an articulated vehicle which comprises:
   a front element and a rear element which are pivotable about a steering linkage disposed between them and
      a distribution box which supplies power from an engine to a forward wheelshaft of the front element via a first shaft and to a rear wheelshaft of the rear element via a second shaft,
   characterised by comprising the following steps:
      the longitudinal differential being disposed between the first shaft and the second shaft,
      a steering angle v formed between the front element and the rear element being detected by a detection means,
      the detection means causing a differential brake for the longitudinal differential to be kept locked when the detection means detects a steering angle v which is smaller than a predetermined steering angle $v_1$, and
      the detection means takes the form of an operating arm of a valve, which operating arm is provided with a guide roller which bears upon an outer contour of a spindle of the steering linkage.

12. The method according to claim 11, further comprising the step of:
   said valve is acted upon by the detection means to raise or lower the oil pressure in a connecting conduit connected to the differential brake in order thereby respectively to lock or disengage the differential brake.

13. The method according to claim 12, further comprising the step of:
   high or low pressure in the connecting conduit acts upon a piston in the differential brake in order respectively to free or lock, or brake, discs in a brake package which respectively disengage from one another or connect the first shaft and the second shaft.

* * * * *